United States Patent [19]
Buscemi

[11] Patent Number: 5,860,948
[45] Date of Patent: *Jan. 19, 1999

[54] APPARATUS AND METHOD FOR TISSUE DEFECT REPAIR BY DEPOSITION

[75] Inventor: Paul J. Buscemi, Long Lake, Minn.

[73] Assignee: Scimed Life Systems, Inc., Maple Grove, Minn.

[ * ] Notice: Under 35 U.S.C. 154(b), the term of this patent shall be extended for 562 days.

[21] Appl. No.: 541,658

[22] Filed: Oct. 2, 1995

Related U.S. Application Data

[63] Continuation of Ser. No. 134,978, Oct. 12, 1993, abandoned.

[51] Int. Cl.$^6$ .................................................. A61M 1/30
[52] U.S. Cl. .............................. 604/21; 604/20; 606/15; 606/16
[58] Field of Search ..................... 433/29, 226; 604/20, 604/21; 606/3, 10, 13–16, 92, 93, 213, 214

[56] References Cited

U.S. PATENT DOCUMENTS

| | | |
|---|---|---|
| 5,035,621 | 7/1991 | Gottschalk et al. ............... 433/226 |
| 5,092,773 | 3/1992 | Levy ............................... 433/224 |
| 5,151,031 | 9/1992 | Levy ............................... 433/226 |
| 5,171,150 | 12/1992 | Levy ............................... 433/226 |
| 5,184,044 | 2/1993 | Thomas .......................... 313/638 |
| 5,207,670 | 5/1993 | Sinofsky ............................. 606/8 |
| 5,209,776 | 5/1993 | Bass et al. . | |
| 5,292,346 | 3/1994 | Leravolo ......................... 607/80 |
| 5,540,677 | 7/1996 | Sinofsky ............................. 606/8 |

Primary Examiner—Wynn Wood Coggins
Assistant Examiner—Cris L. Rodriguez
Attorney, Agent, or Firm—Vidas, Arrett & Steinkraus

[57] ABSTRACT

A catheter apparatus and method is provided for repairing tissue defects intraluminally by depositing a polymerizable material at a tissue defect site and polymerizing the material in situ to effect the build-up of a repair material at the site of a defect. This is accomplished in preferred arrangements by providing a catheter having an optical fiber arranged for the transmission and emission of radiation such as UV at the defect site along with the transmission of the polymerizable material. Contact between the radiation and the coincident delivery of polymerizable material at the site effects a build-up of solid repair material at the defect.

18 Claims, 4 Drawing Sheets

APPARATUS AND METHOD FOR TISSUE DEFECT REPAIR BY DEPOSITION

This is a continuation of application Ser. No. 08/134,978 filed on Oct. 12, 1993 now abandoned.

BACKGROUND OF THE INVENTION

This invention relates to catheter apparatus and method for the deposition of a polymerizable material at a tissue defect site and the in situ polymerization of the material to effect the build-up of a repair material at the defect site.

The term "polymerization" is used herein to include all forms including cross-linking as well as chain extensions.

Utility is found in various body passageways and that term is used herein to include any duct as well as any vein, artery, blood vessel and related parts of vascular systems, although it is not limited thereto.

SUMMARY OF THE INVENTION

In accordance with the invention apparatus and method is provided for depositing a photopolymerizable material at a tissue defect site and polymerizing it in situ. This is accomplished in preferred arrangements by providing a catheter having an optical fiber arranged for the transmission and emission of radiation such as UV at the defect site along with the transmission of the polymerizable material. Contact between the radiation and the coincident delivery of polymerizable material at the site effects a build-up of solid repair material at the defect.

DETAILED DESCRIPTION OF THE INVENTION

Figure 1:
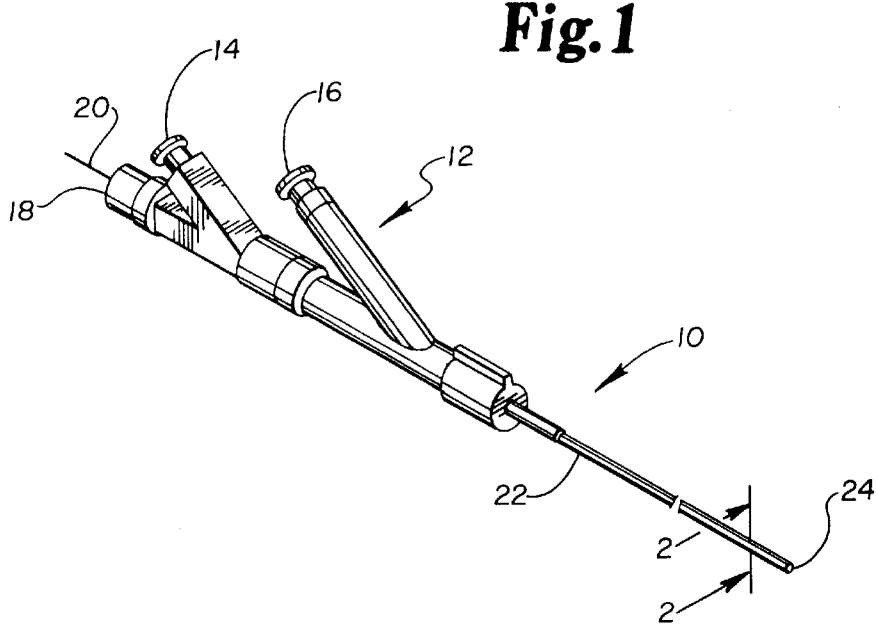
FIG. 1 is an exemplification of a typical catheter which may be used in practicing this invention shown in perspective view.

FIG. 1 illustrates a catheter generally indicated at 10 which is typical structure with some minor modifications to suit the needs of the present invention. It includes a manifold section generally indicated at 12 having two inlet ports 14 and 16 for accepting fluids and a port 18 for accepting an optical fiber 20 in a lumen which extends the length of the catheter body 22 to or near its distal end 24. The catheter may include a guide wire as is known in the art although not shown in the Figure.

Figure 2:
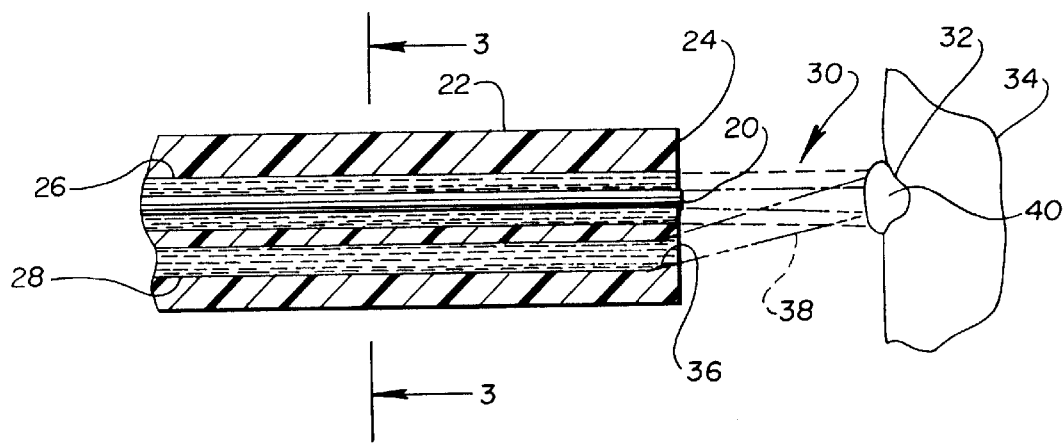
FIG. 2 is a detailed showing of the distal end of the catheter of FIG. 1 showing how it is constructed and arranged to carry out the invention, shown in a longitudinal sectional view along line 2—2.
Figure 3:
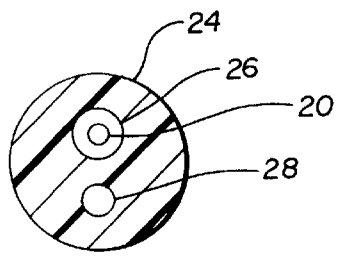
FIG. 3 is a sectional view along line 3—3 of FIG. 2.

Referring now to FIG. 2, the internal construction and arrangement of catheter 10 for the purposes of this invention will be better understood. FIG. 2 is a detail of the distal end 24 of catheter 10 shown in longitudinal cross-section. It includes catheter body 22 which is of a flexible elongate material as is known in the art. At least two lumens 26 and 28 extend the length of the catheter body 22. Lumen 26 communicates with port 14 and lumen 28 communicates with port 16. Also, the optical fiber 20 extends through lumen 26 and is positioned at or near the distal end of the catheter body so as to direct radiation outwardly from the end of the catheter as indicated schematically at 30, the radiation being directed at a defect site 32 in tissue 34.

Lumen 26 also has room to accommodate a flow of a first fluid around the optical fiber 20, the fluid being introduced at port 14 and exiting at the distal end along with the emitted radiation from fiber 20. The purpose of the fluid is to act as a light guide means for the radiation such as UV which is emitted by optical fiber 20. This arrangement is sometimes referred to in the art as a fluid light core. The proximal end of fiber 20 may be connected to a radiation source (not shown) such as UV laser as is known in the art. One such device is described in an article included in July/August 1988 issue of *Gastrointestinal Endoscopy* for a ND:YAG Laser. The fluid of the fluid light core also clears away blood and other body fluids. A basic requirement for the fluid light guide or core is that the index of refraction of the guide fluid or first fluid be higher than that of the surrounding medium so that internal reflection occurs. In this case, the surrounding medium is likely to be blood or other body fluids, blood having an index of refraction of about 1.3. Fluid media for the light guide having an index of refraction above 1.3 includes most organic fluids. Examples of such fluids are dimethyl sulfoxide, ethylene glycol, butyl stearate and ethyl acetate.

Lumen 28 functions to accept and carry a flow of a second fluid including a polymerizable material which is introduced at port 16. The distal end of lumen 28 is arranged to direct the fluid flow to the targeted defect site as in the fluid core. For example, it may be configured as shown at 36 to angularly direct the fluid and polymerizable material to the target site as shown at 38 and intercept the flow 30 and the emitted radiation. The coincidence of radiation and polymerizable material in the proximity of the defect site 32 results in the in situ polymerization of the material and a solid build-up 40 thereof to fill and or cover the defect in the tissue.

Examples of the polymerizable material are copolymers of PEO) and methyl methacrylate in saline with the initiator Azobisisobutyronitrile (AIBN). Additionally, aqueous solutions of dimethyl sulfoxide (DMSO), saline, acetonitrile, alcohols and combinations of these may be used, as well as others such as diethylene glycol diacrylate, neopentyl glycol diacrylate, isobornyl methacrylate and the like.

Material in polymerizable forms may be in the shape of nanoparticles (10–1000 nanometers) which carry photoactivatable groups on their surface or in the form of macromolecules which have active sides chains or active groups in their main chains. Examples include: polyacrylamide leads or collagen beads having vinyl groups on the surface or acrylate groups or epoxide groups on the surface. Also, polyethylene oxide (PEO) or collagen or polylactide macromolecules having vinyl groups, acrylate groups or epoxide groups in main or side chains may be used.

Reactive chemicals to effect build-up and repair, such as acrylics or high MW acrylics or PEO, may also be included in the first fluid or light guide. Whether or not they absorb light will depend on the nature of the particular chemical reaction envisioned and the speed of the reaction required. If UV radiation were utilized in the range of 200–350 nm and reactive components such as fluoresceine were included, absorbed radiation could cause reactions to initiate in the stream. This could be useful for filling deep defects. Care would have to be taken to insure that reactive components did not alter the total index of refraction of the light guide stream to cause the loss of total internal reflection.

Examples of polymerizable materials which may also be utilized in the fluid core are acrylate containing compounds such as diethylene glycol diacrylate, neopentyl glycol diacrylate, isobornyl methacrylate, and copolymers of any of these with nonreactive side chains such as polyethylene glycol 600 or biodegradable materials such as collagen or carbohydrates.

Epoxide groups copolymerized with hydrophilic polymers can be dispersed in either the fluid reaction or polymerizable stream or both, while amine or hydroxy moieties also containing light absorbing components tuned to the wavelength of the light source could be present in the fluid light core. While reactions of expoxides and amines is relatively quick in bulk, and epoxide-hydroxy reactions are relatively slow without catalysts, both reactions would occur quickly under the influence of radiation. Those components not in the vicinity of the radiation would diffuse into blood and be too dilute to react. If the light were focused on to the surface of tissue, then the surface would be the primary area of reaction.

Another version of the reactive species, carried either in the fluid light stream or in the reactive species polymerizable stream, could include molecules that contain very hydrophobic residues such that these components have a great tendency to adsorb to surfaces but not to react until exposed to light. Such multiple hydrophobic segments as aliphatic chains, chains of amino acids as multiple repeats of glycine plus phenylalanine or tyrosine, porphyrin containing chains could be used to absorb to lipid containing areas of tissue. Some of these hydrophobic moieties could also be used to absorb radiation.

In a preferred form the second fluid will be selected of such a color as to absorb the radiation emitted by the fiber. For example, in the case of UV radiation, saline solution fluid could be selected for this purpose.

The second fluid carrying the reactive polymerizable groups will be selected not only for its capacity for solubility of those reactive groups or molecules but also for its ability to transfer radiation to those groups. The second fluid may contain components which absorb radiation below the activating wavelength of the photocrosslinking group. In this case the absorbing group could absorb radiation and subsequently fluoresce at a higher wavelength. In this manner the efficiency of absorbing local radiation may be maintained to a higher degree if the absorption efficiency of the initial group was higher than that of the reactive group.

The reactive stream or second fluid may contain as well molecules that absorb radiation at the wavelength of the impinging light to enhance reactivity at the pathcrossing of the fluid light stream and the reactive carrier stream. This fluid stream may be simply saline solution, aqueous solutions of aliphatic alcohols or DMSO or other biologically tolerated organic materials. It may contain ultraviolet absorbing dyes.

In another method to enhance efficiency, particles which may not necessarily be a direct part of the chemical reaction may be used to scatter light in the general vicinity of the reactive species and cause their conversion to a crosslinked material. The particle size for light scattering must be on the order of no less than ¼ of the wavelength of the light used otherwise, the light will not scatter from these particles. This is a particular advantage if a lower wavelength light is used to fluoresce a compound, the advantage being that smaller particles would have less of a tendency to coagulate or block arteries. A lower wavelength allows the use of smaller particles.

These particles may also be part of the reactive process such that the reactive groups may be placed onto such particles which also serve to scatter light as well as serving to provide structural building blocks. Such particles may be made of carbohydrates such as chitosan, dirmatan sulfate, latexes, collagen, albumin, polyesters or other materials.

One may use liquids of differing index of refraction to alter the scattering properties. While mixing will of course occur from two impinging streams or from two concentric streams that are impinging on a surface, if the second polymer carrying stream has a substantially different index, then the directions of the light will be altered or refracted in the area of mixing more so than if two liquids of the same index of refraction were mixed.

Figure 9:
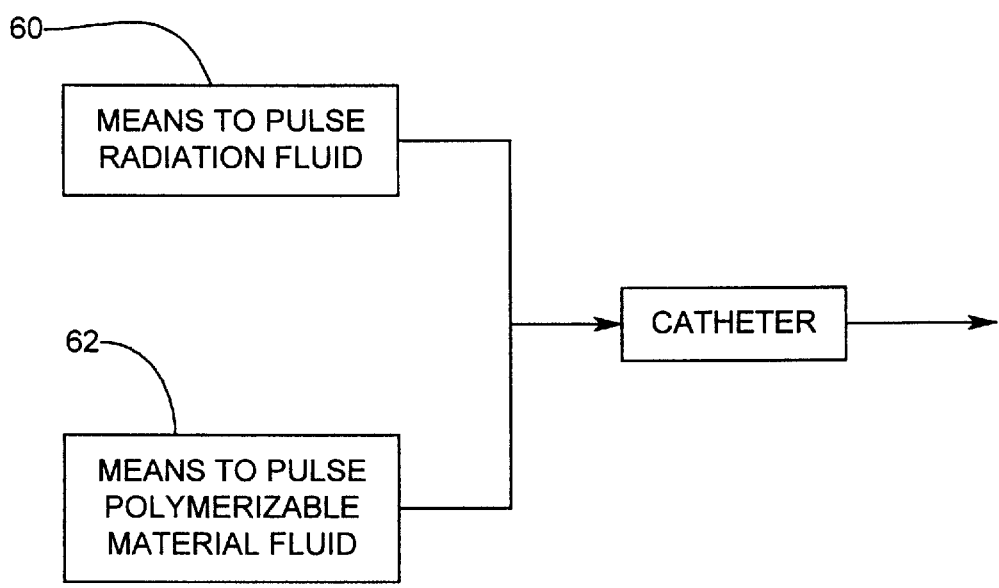
FIG. 9 is an schematic showing the pulsing of the radiation fluid and the pulsing of polymerizable material fluid.

Various other arrangements are possible. For example, one may utilize differing refractions of index for the two fluids or the radiation fluid may be pulsed as shown at 60 in FIG. 9 and polymerizable material fluid may be pulsed as shown at 62 in FIG. 9, so as to produce a finite time period between the two pulses to better assure polymerization and build-up at the defect site. Such pulsing arrangements are known in the art.

Figure 4:
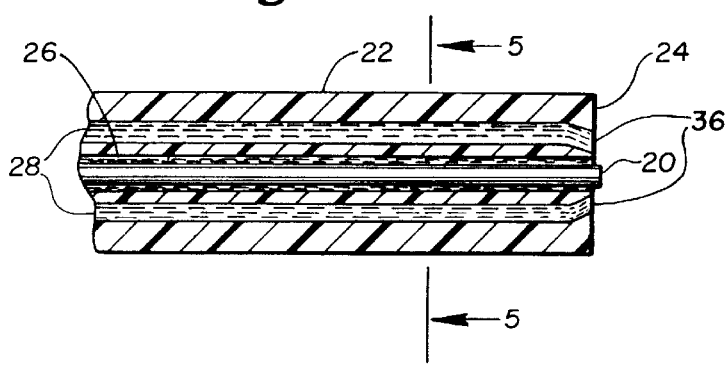
FIG. 4 is an alternate embodiment of the catheter in sectional view similar to that of FIG. 2.
Figure 5:
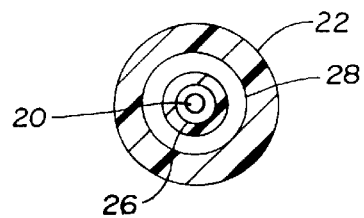
FIG. 5 is a cross-sectional view taken along lines 5—5 of FIG. 4.

Referring now to FIGS. 4 and 5, another embodiment of the catheter construction is shown in which lumen 28 is of an annular configuration surrounding lumen 26. Such a coaxial arrangement may be preferred in some instances.

Figure 6:
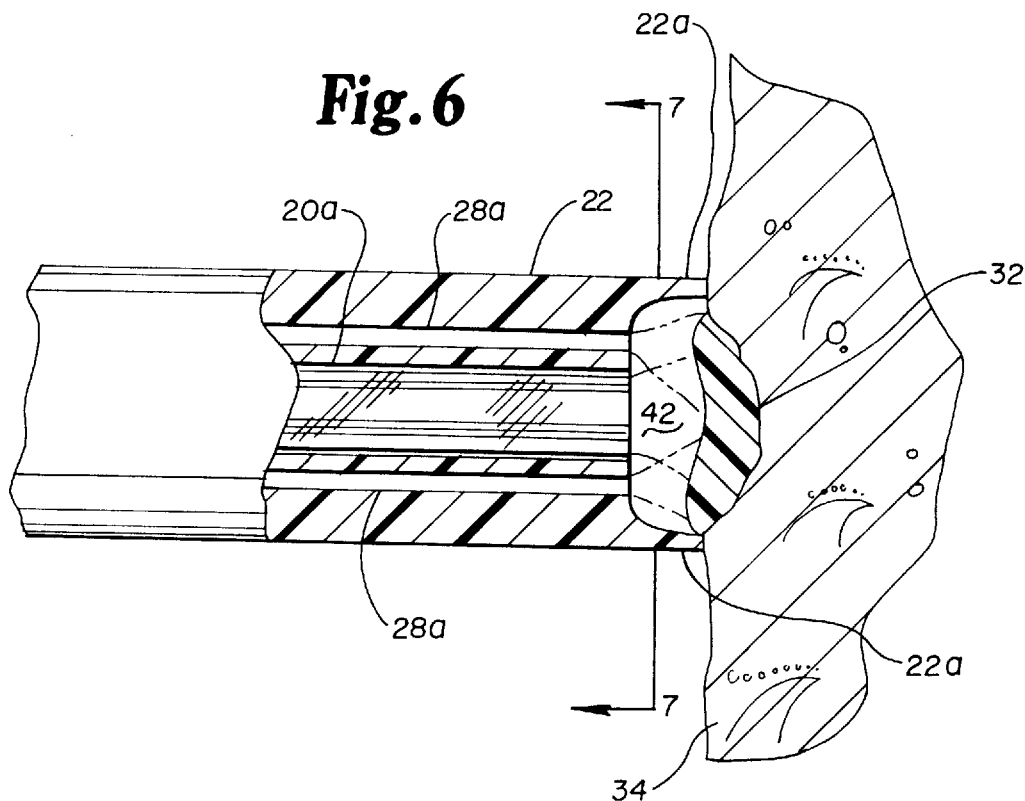
FIG. 6 is another embodiment of the invention.
Figure 7:
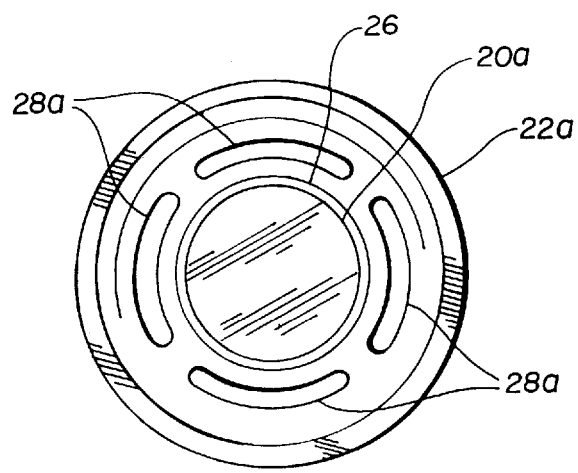
FIG. 7 is a cross-sectional view along line 7—7 of FIG. 6.

Yet another embodiment is shown in FIGS. 6 and 7 which includes a plurality of lumens 28a distributed around a central lumen 26 carrying a large area optical fiber bundle 20a. The end of catheter 22 is modified to include an open ended cup-like end portion 22a which may be placed against tissue 34 at a defect site 32 as shown to enclose same and form a chamber 42. Polymerizable material delivered through lumens 28a fill chamber 42 and radiation emitted from the optical bundle 20a polymerizes the material substantially all at once to form a large built-up repair.

Figure 8:
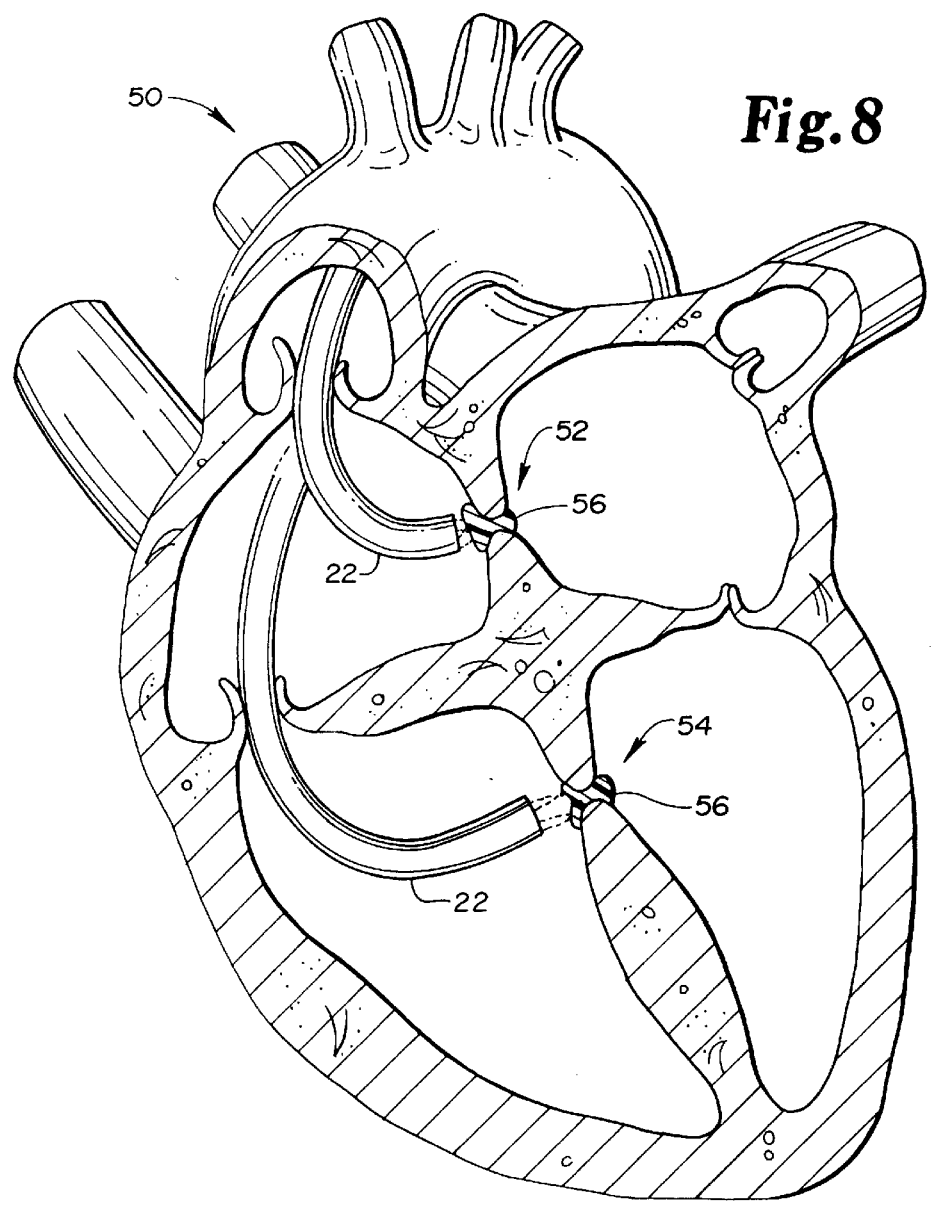
FIG. 8 is a pictorial diagram showing the practice of the invention in repairing heart defects.

Referring now to FIG. 8, the use of the invention in repairing septal defects is illustrated in two separate heart locations. A heart generally indicated at 50 might have a septal defect as indicated generally at 52 or at 54. Such a defect may be repaired intraluminally by the introduction of catheter 22 at either of the locations 52 or 54 to cause a build-up of solid repair material 56 as shown.

While this invention may be embodied in may different forms, there are described in detail herein specific preferred embodiments of the invention. This description is an exemplification of the principles of the invention and is not intended to limit the invention to the particular embodiments illustrated. For example, two separate catheters may be utilized instead of the integrated catheter structure shown.

What is claimed is as follows:

1. A catheter in combination with a source of photocurable soft tissue repair material, the catheter having proximal and distal ends, said catheter further comprising:
   a) a manifold section having at least one fluid inlet port and an optical fiber inlet port;
   b) a catheter body comprising at least two lumens:
      i) a first of said at least two lumens communicating with one of said at least one fluid inlet ports; and ii) a second of said at least two lumens comprising a fluid light core communicating with one of said at least one fluid inlet ports and the optical fiber inlet port;

d) delivery means in association with one of said at least one fluid inlet ports and the first of said at least two lumens of the catheter body for delivering photocurable soft tissue repair material to a targeted soft tissue defect site located in a duct, vein, artery, or blood vessel, said photocurable soft tissue repair material being suitable for deposition at the soft tissue defect site; and e) means for transmission and emission of radiation associated with the fluid light core and the optical fiber inlet port, said means comprising an optical fiber, whereby the photocurable soft tissue repair material may be delivered to the tissue defect site and the radiation of the fluid light core may be utilized to polymerize the repair material at the soft tissue defect site.

2. A catheter in combination with a source of photocurable soft tissue repair material, the catheter having a proximal end, an open-ended cup-like distal end, said catheter further comprising:

a) a fluid light core;

b) a manifold section having at least two fluid inlet ports and an optical fiber inlet port; and c) a catheter body comprising:

i) at least two lumens, a first of said at least two lumens communicating with a first of said at least two fluid inlet ports and a second of said at least two lumens comprising the fluid light core communicating with a second of said at least two fluid inlet ports and the optical fiber inlet port;

ii) delivery means in association with the first of said at least two fluid inlet ports and the first of said at least two lumens of the catheter body for delivering photocurable soft tissue repair material to a targeted soft tissue defect site located in a duct, vein, artery, or blood vessel, said photocurable soft tissue repair material being suitable for deposition at the tissue defect site;

d) means for transmission and emission of radiation comprising an optical fiber associated with the fluid light core, whereby the photocurable soft tissue repair material may be delivered to the tissue defect site and the radiation of the fluid light core may be utilized to polymerize the repair material at the soft tissue defect site.

3. A catheter constructed and arranged for insertion into vessels, ducts, veins, arteries, or blood vessels of a living body, the catheter having a proximal end portion, a distal end portion, an interior and an exterior, said catheter further including:

optical fiber means located in the interior portion of the catheter, for emitting radiation at the distal end portion of the catheter toward a soft tissue target site in the body, located in a body passageway, duct, vein, artery, or blood;

fluid light guide means positioned within the catheter relative to the optical fiber so as to direct the radiation emitted by the fiber toward the target site, said fluid light guide means comprising a fluid having an index of refraction greater than about 1.3, and a supply of photocurable fluid soft tissue repair material associated with the catheter, said photocurable material being suitable for deposition at the target site, and means located within the catheter for delivery of same to the target site whereby radiation emitted from the fiber intercepts the photocurable fluid in the vicinity of the soft tissue target site to effect build-up of solid soft tissue repair material at the soft tissue site.

4. The catheter construction of claim 3 including a first lumen for carrying the optical fiber and the fluid light guide means and a second lumen for carrying the photocurable fluid.

5. A catheter constructed and arranged for insertion into vessels, ducts, veins, arteries, or blood vessels of a living body, the catheter having a proximal end portion, a distal end portion, an interior and an exterior, said catheter further including:

optical fiber means located in the interior portion of the catheter, for emitting radiation at the distal end portion of the catheter toward a soft tissue target site in the body, located in a body passageway, duct, vein, artery, or blood;

fluid light guide means positioned within the catheter relative to the optical fiber so as to direct the radiation emitted by the fiber toward the target site, said fluid light guide means comprising a fluid having an index of refraction higher than that of blood, and a supply of photocurable fluid soft tissue repair material associated with the catheter, said photocurable material being suitable for deposition at the target site, and means located within the catheter for delivery of same to the target site whereby radiation emitted from the fiber intercepts the photocurable fluid in the vicinity of the soft tissue target site to effect build-up of solid soft tissue repair material at the soft tissue site.

6. The catheter construction of claim 5 wherein the photocurable fluid material is of a color selected to absorb the radiation emitted by the fiber.

7. The catheter construction of claim 6 wherein the photocurable fluid material has a lower index of refraction for UV light than the light guide fluid.

8. A catheter constructed and arranged for insertion into vessels, ducts, veins, arteries, or blood vessels of a living body, the catheter having a proximal end portion, a distal end portion, an interior and an exterior, said catheter further including:

optical fiber means located in the interior portion of the catheter, for emitting radiation at the distal end portion of the catheter toward a soft tissue target site in the body, located in a body passageway, duct, vein, artery, or blood;

means for pulsing the radiation emitted by the optical fiber means located in the interior portion of the catheter;

fluid light guide means positioned within the catheter relative to the optical fiber so as to direct the radiation emitted by the fiber toward the target site, and a supply of photocurable fluid soft tissue repair material associated with the catheter, said photocurable material being suitable for deposition at the target site, means located within the catheter for delivery of same to the target site, and means for pulsing the delivery of the photocurable fluid soft tissue repair material associated with the catheter, whereby radiation emitted from the fiber intercepts the photocurable fluid in the vicinity of the soft tissue target site to effect build-up of solid soft tissue repair material at the soft tissue site.

9. A catheter constructed and arranged for insertion into cavities, vessels and the like of a living body, the catheter having a proximal end portion, an open-ended cup-like distal end portion, an interior and an exterior, said catheter further including:

optical fiber means located in the interior portion of the catheter, for emitting radiation at the distal end portion of the catheter toward a target site in the body;

light guide means positioned within the catheter relative to the optical fiber so as to direct the radiation emitted by the fiber toward the target site, and a supply of photocurable fluid material associated with the catheter and means for delivery of same to the target site located within the catheter whereby radiation emitted from the fiber intercepts the photocurable fluid in the vicinity of the target site to effect build-up of solid repair material at the site.

10. A method for building-up a solid soft tissue repair material in a living body in situ at a selected soft tissue target site located in a duct, vein, artery, or blood vessel, the method comprising:

directing a photocurable material suitable for deposition at the soft tissue target site to a selected target soft tissue repair site, and directing radiation to the site for intercepting the photocurable material to initiate photocuring of the material in situ whereby a repair build-up of solid material occurs at the soft tissue site.

11. The method of claim 10 wherein light guide means is used to aid in directing the radiation to the target site.

12. The method of claim 11 wherein the light guide means comprises a fluid.

13. The method of claim 12 wherein the radiation is transmitted by means of an optical fiber in a catheter and the light guide fluid is transmitted through a lumen in the catheter.

14. The method of claim 13 wherein the fiber and light guide fluid are in the same lumen.

15. The method of claim 13 wherein the photocurable material is a fluid which is transmitted through another lumen in the catheter.

16. The method of claim 13 wherein the radiation is UV.

17. An intraluminal method for building-up a solid repair material in a living body in situ at a selected target site, comprising:

directing a photocurable material to a selected target repair site, and using a light guide fluid transmitted through a lumen in a catheter to direct radiation transmitted by means of an optical fiber in the catheter to the target site for intercepting the photocurable material to initiate photocuring of the material in situ whereby a repair build-up of solid material occurs at the site.

18. The method of claim 10 wherein two separate catheters are utilized, one catheter for directing the photocurable material to the selected target repair site, and another catheter for directing radiation to the site for intercepting the photocurable material to initiate photocuring of the material in situ whereby a repair build-up of solid material occurs at the site.

* * * * *